United States Patent
Chappuis

(10) Patent No.: US 10,390,860 B2
(45) Date of Patent: Aug. 27, 2019

(54) INTERNAL PEDICLE INSULATOR

(71) Applicant: James L. Chappuis, Atlanta, GA (US)

(72) Inventor: James L. Chappuis, Atlanta, GA (US)

(73) Assignee: CHAP-MED, INC., Destin, FL (US)

( * ) Notice: Subject to any disclaimer, the term of this patent is extended or adjusted under 35 U.S.C. 154(b) by 0 days.

(21) Appl. No.: 15/975,308

(22) Filed: May 9, 2018

(65) Prior Publication Data
US 2018/0256211 A1 Sep. 13, 2018

Related U.S. Application Data

(63) Continuation of application No. 14/723,620, filed on May 28, 2015, now Pat. No. 9,993,268.

(60) Provisional application No. 62/003,978, filed on May 28, 2014.

(51) Int. Cl.
*A61B 17/68* (2006.01)

(52) U.S. Cl.
CPC .................................. *A61B 17/686* (2013.01)

(58) Field of Classification Search
CPC .................................................. A61B 17/686
See application file for complete search history.

(56) References Cited

U.S. PATENT DOCUMENTS

| | | | |
|---|---|---|---|
| 5,501,557 A * | 3/1996 | Wakai | F16B 13/124 411/55 |
| 5,688,090 A * | 11/1997 | Miyamoto | F16B 13/124 411/55 |
| 5,749,688 A * | 5/1998 | Wakai | F16B 13/124 411/42 |
| 6,093,207 A | 7/2000 | Pisharodi | |
| 6,306,156 B1 | 10/2001 | Clark | |
| 6,506,008 B2 | 1/2003 | Merkli | |
| 7,083,621 B2 | 8/2006 | Shaolian et al. | |
| 7,338,500 B2 * | 3/2008 | Chappuis | A61B 17/686 411/80.5 |
| 7,686,555 B1 * | 3/2010 | Larson | F16B 2/14 411/349 |
| 8,900,236 B2 * | 12/2014 | Chappuis | A61B 17/686 606/86 R |
| 8,956,394 B1 * | 2/2015 | McDonnell | A61B 17/686 606/300 |
| 2004/0267277 A1 | 12/2004 | Zannis et al. | |
| 2005/0216012 A1 * | 9/2005 | Willmen | A61B 17/686 606/323 |
| 2005/0240194 A1 * | 10/2005 | Chappuis | A61B 17/686 606/86 R |
| 2006/0095040 A1 * | 5/2006 | Schlienger | A61B 17/686 606/64 |

(Continued)

*Primary Examiner* — Eric S Gibson
(74) *Attorney, Agent, or Firm* — Morris, Manning & Martin, LLP; Bryan D. Stewart

(57) ABSTRACT

A pedicle insulator implant is designed to protect the nerves and surrounding tissue from injury by pedicle screws or other surgical devices and instruments. In its basic structure, the implant has a thicker section and a thinner section, the thicker section providing protection for nerves and other sensitive tissues while the thinner section can be deformable and provides grip. In one variation of the basic structure, the thinner section possess a rough surface when it is desirable in situations to provide further grip of the assembly and prevent rotation during the insertion of, for example, a pedicle screw.

10 Claims, 2 Drawing Sheets

(56) References Cited

U.S. PATENT DOCUMENTS

| | | | |
|---|---|---|---|
| 2007/0118131 A1* | 5/2007 | Gooch | A61B 17/686 606/328 |
| 2007/0219553 A1* | 9/2007 | Chappuis | A61B 17/686 606/86 A |
| 2008/0221623 A1* | 9/2008 | Gooch | A61B 17/686 606/302 |
| 2008/0221624 A1* | 9/2008 | Gooch | A61B 17/686 606/302 |
| 2011/0106177 A1* | 5/2011 | Lewis | A61B 17/686 606/305 |
| 2012/0203226 A1* | 8/2012 | Schlienger | A61B 17/686 606/64 |
| 2015/0045841 A1* | 2/2015 | Oglaza | A61B 17/686 606/322 |
| 2015/0105830 A1* | 4/2015 | Biedermann | A61B 17/8685 606/317 |
| 2015/0150557 A1* | 6/2015 | Tsai | A61B 17/686 606/151 |
| 2015/0342644 A1* | 12/2015 | Chappuis | A61B 17/686 606/86 R |
| 2016/0038206 A1* | 2/2016 | McDonnell | A61B 17/686 606/322 |
| 2016/0074072 A1* | 3/2016 | McDonnell | A61B 50/30 606/104 |
| 2016/0128735 A1* | 5/2016 | Suddaby | A61B 17/66 606/263 |
| 2017/0128100 A1* | 5/2017 | Jones | A61B 17/686 |
| 2017/0215934 A1* | 8/2017 | McDonnell | A61B 17/686 |

* cited by examiner

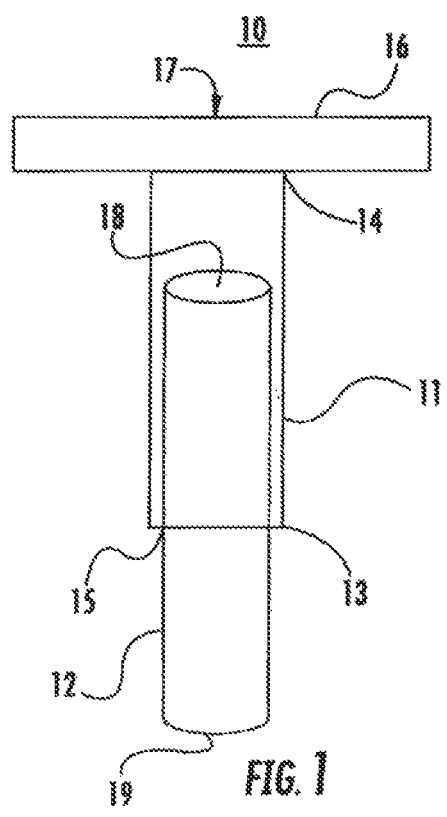
FIG. 1
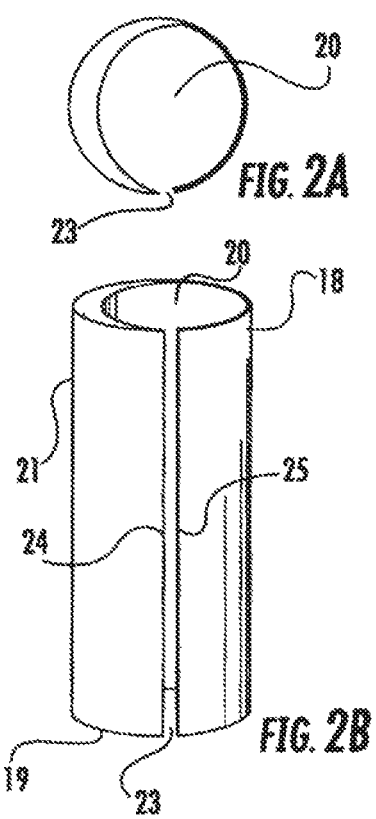
FIG. 2A
FIG. 2B
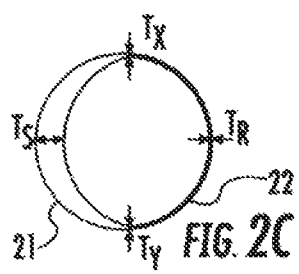
FIG. 2C
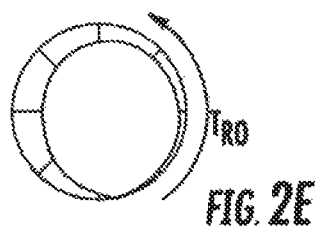
FIG. 2E
FIG. 2G
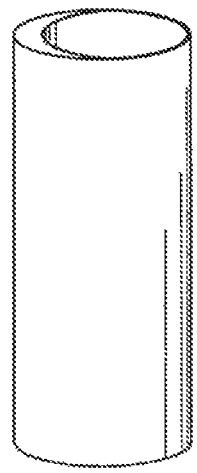
FIG. 2D
FIG. 2F
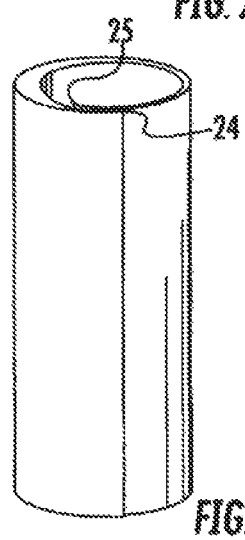
FIG. 2H

INTERNAL PEDICLE INSULATOR

CROSS REFERENCE TO RELATED APPLICATIONS

This application is a continuation of, and claims priority to, U.S. patent application Ser. No. 14/723,620, filed May 28, 2015, entitled "INTERNAL PEDICLE INSULATOR" which claims the benefit of and priority to U.S. Provisional Patent Application No. 62/003,978, entitled "INTERNAL PEDICLE INSULATOR", filed May 28, 2014. The application is related to U.S. patent application Ser. No. 11/712,257 which is a Continuation in Part of U.S. Pat. No. 7,338,500. The contents of the above referenced applications are incorporated herein by reference in their entireties.

FIELD OF THE INVENTION

This invention relates to surgical instruments and tools. In particular, pedicle insulator assemblies and methods of insertion are described.

BACKGROUND

Spinal fusion typically involves the removal of damaged disc material between two adjacent vertebrae and the subsequent insertion of one or more interbody devices into the emptied disc space, either using an anterior or a posterior approach. In order to ensure primary stability, the surgeon usually adopts a fixation system that is anchored to the spine by means of orthopedic screws implanted into the pedicles of the vertebrae that are to be fused together. The single screws are connected together by means of rigid or semi-rigid rods, which are conveniently housed within a transversal hole provided in the screw head.

Since the FDA approval of pedicle screws, approximately 200,000 instrumented fusions occur each year in the US. There is very limited tolerance between the pedicle screw and the nerve root with the inferomedial wall of the pedicle (approx 1-2 mm). Current minimally invasive techniques increase risk of malposition. The pedicle screw may be inserted off center, such as, for example, too medial, which may impinge on the associated nerve root causing pain. This requires a repositioning of the screw. However, even after repositioning there may be an effect on the pedicle wall, which can still cause nerve root irritation. Such procedures are also susceptible to loosening of the screw.

SUMMARY OF THE INVENTION

Embodiments of the invention are directed to an internal pedicle insulator implant assemblies and related methods. In this regard, an exemplary embodiment of an internal pedicle insulator implant comprises: a cylindrical wall defining an interior cavity and having a first end and a second end, the cylindrical wall comprising a smooth, non threaded segment, a rough surface segment, or combinations thereof. In some embodiments, one segment of the wall is of a greater thickness than other segments of the wall; whereby the pedicle insulator implant shields a pedicle screw that is implanted into the vertebral body and reduces nerve root irritation and diminishes the loosening of the pedicle screw.

Accordingly, it is an objective of this invention to provide an internal pedicle insulator implant assembly for shielding a pedicle screw that is implanted into the vertebral body for reducing nerve root irritation and diminishing the loosening of the pedicle screw.

It is also another objective to provide methods for stabilizing a surgical fixture Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

The invention can be better understood with reference to the following drawings. The components in the drawings ire not necessarily to scale, emphasis instead being placed upon clearly illustrating the principles of the present invention. Moreover, in the drawings, like reference numerals designate corresponding parts throughout the several views.

FIG. 1 is a perspective view of a pedicle insulator implant assembly.

FIG. 2A is a top view showing an embodiment of the cylindrical wall.

FIG. 2B is the side view of FIG. 2A.

FIG. 2C is a top view showing another embodiment of the cylindrical wall.

FIG. 2D is the side view of FIG. 2C.

FIG. 2E is a top view showing a further embodiment of the cylindrical wall.

FIG. 2F is the side view of FIG. 2E.

FIG. 2G is a lop view showing yet a further embodiment of the cylindrical wall.

FIG. 2H is the side view of FIG. 2G.

DETAILED DESCRIPTION OF THE PREFERRED EMBODIMENT

Figure 3A:
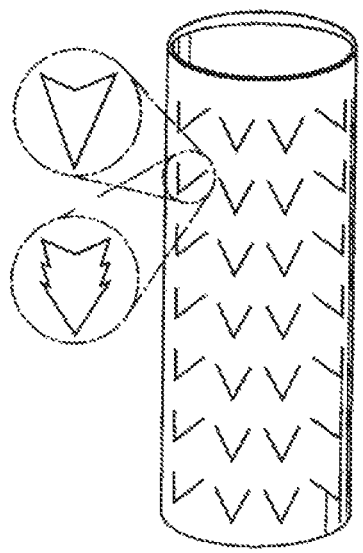
FIGS. 3A-3C are segment views showing various embodiments of the rough segment of the cylindrical wall.
Figure 3B:
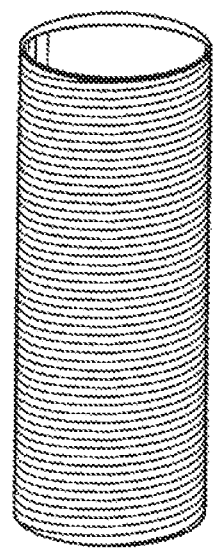

The following description of the preferred embodiments is merely exemplary in nature and is in no way intended to limit the invention, its application or uses. Embodiments of the invention may be practiced without the theoretical aspects presented. Moreover, the theoretical aspects are presented with the understanding that Applicants do not seek to be bound by the theory presented.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range Where the stated range includes one or both of the limits, ranges excluding either or both of those included limits are also included in the invention.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the term "segment" is used to denote a geometric section of the cylinder. For example, if the height of the cylinder is denoted as h, and the half-axes, equal to the radius in the case of an round cylinder, are denoted as α and β, the angle between them, denoted as γ, would represent the size of the "segment". The larger the value of γ, the larger the segment which can encompass the entire height of the cylinder or parts thereof. For example, the segment may taper off such that the top end of the cylinder has a thicker wall than the bottom end of the cylinder. Standard mathematical equations can be used to calculate surface areas, volumes, etc.

As used herein, the term "cylinder" is used to encompass any cylindrical geometry, e.g. parabolic, elliptic or hyperbolic geometries.

As used herein the term "method" refers to manners, means, techniques and procedures for accomplishing a given task including, but not limited to, those manners, means, techniques and procedures either known to. or readily developed from known manners, means, techniques and procedures by practitioners of the chemical, pharmacological, biological, biochemical and medical arts.

Throughout this application, various embodiments of this invention may be presented in a range format It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3,4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Pedicle Insulator Implant

Embodiments of the invention are directed to a pedicle insulator implant. The implant is designed to protect the nerves and surrounding tissue from injury by pedicle screws or other surgical devices and instruments. In some embodiments, the implant comprises both a rough and smooth surface area on opposing segments of the implant. The rough surface area is desirable in situations to provide further grip of the assembly and prevent rotation during the insertion of, for example, a pedicle screw. In other embodiments, the insulator implant comprises a segment of the implant having a thicker wall which is positioned between the pedicle and nerve.

With the advent of pedicle screw technology none of the devices provide protection when inserted into a patient. There is very limited tolerance between neural structures and a pedicle screw since the inferomedial aspect of the pedicle is an area of neural structures and hence a "danger zone." There is only a 1-3 mm between a nerve root and a pedicle screw. In addition a lateral breach compromises fixation. Due to the very small margin of error, many pedicle screw implantations result in the malposition of the screw.

Pedicle screws also become loose over a period of time. This is very common in elderly who are osteoporotic (44 million currently at risk in the U.S.) and also as the aging population is more active resulting in a demand for more extensive procedures. Lateral breaches compromise fixation which creates loosening and pseudarthrosis results when constructs loosen over time. Most pedicle screws are left in permanently, not temporarily as approved by the FDA, which can result in loosening over time. Some of the traditional pedicle screws have rods resulting in increased number of problems, for example, with long constructs for degenerative scoliosis or with distraction to correct deformities. The pedicle insulator embodied herein is designed to overcome these and other problems and disadvantages associated with pedicle screws.

In some embodiments, the implant comprises one or more biocompatible or inert materials. For example, the segment having a greater thickness may comprise a "softer"smoother material than another segment. In other embodiments, the implant is uniform in the type of material used. Examples of materials include without limitation: titanium, or any conventional material used for surgical implants, such as stainless steel and its many different alloys, titanium alloys, metallic alloys, polymeric materials, plastics, plastic composites, ceramic and any other metal or material with the requisite strength and biologically inert properties. However, it is to be understood, that the various parts of the implant may be constructed from various materials. For example, the segment laving a thicker wall may be made from a material that provides the requisite strength but also flexibility, whereas another segment may be made from a rigid material. In some embodiments, the insulator implant may comprise one or more layers of materials, such as, for example, plastic, polymers, metals or any other biocompatible conventional materials). In other embodiments, the implant may be coated with a biocompatible material, for example, medical grade thermoplastic elastomeric compounds. In other embodiments, the insulator implant comprises polyether ether ketone (PEEK) or a composite of PEEK.

FIGS. 1 through 5 which are now referenced, illustrate the present invention and the manner in which it is assembled. Like reference numerals refer to like components in the various figures. FIG. 1 shows one embodiment of an internal pedicle insulator apparatus 10. The internal pedicle insulator apparatus 10 comprises an outer insertion rod 11, and an internal pedicle insulator implant 12. A fixture sized and shaped can be inserted within the cavity 20 defined by an inwardly facing surface of the pedicle insulator implant. In some embodiments, the pedicle insulator is curvilinear having a radius of about 10 degrees to 360 degrees and any degree therebetween. In other embodiments, the pedicle insulator is curvilinear having a radius of about 120 degrees to about 180 degrees and any degree therebetween.

The outer insertion rod 11 has a lower end 13 and an opposing upper end 14. An opening 15 is disposed at the lower end 13. An optional handle 16 can be disposed toward the upper end 14 of the outer insertion rod 11 to facilitate use of the internal pedicle insulator apparatus 10. An opening at the upper end 14 of the outer insertion rod 11 through which the pedicle insulator implant 12 can pass can also be included (not shown). It is preferable that the outer insertion rod 11 has a substantially round cross-section. It should be noted, however, that the outer insertion rod 11 can comprise any suitable cross-section. The outer insertion rod 11 can comprise titanium, however, it should be understood that the outer insertion rod 11 can comprise any suitable material.

The outer insertion rod 11 is arranged and configured to receive the pedicle insulator implant 12 through the opening 15 disposed at the lower end 13 of the outer insertion rod 11. The pedicle insulator implant 12 is preferably slidably inserted into the outer insertion rod 11 such that the upper end 14 of the outer insertion rod 11 substantially corresponds to the top end 18 of the pedicle insulator implant 12. Similarly, the lower end 13 of the outer insertion rod 11 substantially corresponds with the bottom end 19 of the pedicle insulator implant 12. The pedicle insulator implant 12 is laterally slidable within the outer insertion rod 11.

In one embodiment, a pedicle insulator implant, implantable in a vertebral body of a spine, comprises a cylindrical wall 12 defining an interior cavity 20 and hiving a first end 18 and a second end 19. In some embodiments, the length of the implant it from about 5 mm to about 40 mm from the first end 18 to the second end 19. In other embodiments, the insulator implant is about 10 mm to about 20 mm in length from the first end 18 to the second end 19.

The cylindrical wall 12 comprises a smooth, non threaded segment 21 and a rough surface segment 22, or, the cylindrical wall is uniformly smooth. In embodiments, a segment of the cylindrical wall is thicker in width than the rest of the cylindrical wall. In some embodiments, the segment of the cylindrical wall having a smooth surface is of a greater thickness than the segment having a rough surface. Referring to FIGS. 2A-2H, whereby the thickness of the wall comprising the smooth segment is denoted $T_S$ and the thickness of the wall of the rough segment is denoted $T_R$, $T_S$ is always greater than $T_R$. In some embodiments, the thickness of the wall of a segment of the smooth surface $T_S$ is uniform in width, but thicker than the rest of the wall. In other embodiments, the thickness $T_S$ is greatest at the midpoint of the smooth segment. If this point is denoted $T_{SO}$ the thickness of the wall decreases as the rough segment of the wall is approached. These thicknesses are denoted $T_{SX}$ find $T_{SY}$ and define the point wherein the width of wall is equal to the thickness of the wall having a rough surface. In this embodiment, $T_{SO} > T_{SX}$ $T_{SO} > T_{SY}$ and $T_{SX} = T_{SY} = T_R$. (FIGS. 2A, 2C). In other embodiments, the thickness of one segment of the cylindrical wall increases gradually in thickness $T_R$ so that the thickness of the wall at either $T_Y$ or $T_X$ is greater than the thickness $T_R$ (FIG. 2C). In FIG. 2E, the thickness of the wall increases gradually from $T_{RO}$ the thickness of origin.

In another embodiment, the cylindrical segment comprises a smooth and non-threaded surface directed inwardly and outwardly (FIG. 2C). The thickness of the wall of one segment $T_R$ is less than the thickness of the wall on the opposing segment $T_S$. The thicker segment of the wall is the side of the cylindrical wall which would shield a nerve or other tissue from damage while the thinner segment of the wall allows for the pedicle screw to deform the thinner wall segment as the pedicle screw is driven into the bone. The sizes of each segment of a wall can vary. In some embodiments the thicker segment surface area is equal to the thinner segment surface area. In other embodiments, the thicker segment surface area is greater than the surface area of the thinner segment. In other embodiments, the surface area of the thinner segment of the wall is greater than the surface area of the segment with the thicker wall. In other embodiments, the cylindrical wall comprising the smooth, non threaded surface comprises at least about 25% of the cylindrical wall surface area. In another embodiment, the segment of the cylindrical wall comprising the smooth, non threaded surface comprises at least about 25% of the cylindrical wall surface area.

In other embodiments, the cylindrical wall is non-continuous and comprises a longitudinal slot 23 extending between the first end IS and the second end 19, the longitudinal slot forming opposing sides 24 and 25, each opposing side 24, 25 ending facing each other (FIG. 2A).

In mother embodiment, the cylindrical wall is non-continuous and the opposing segments 24, 25 of the cylindrical wall overlap each other, the one segment extending into the interior cavity 20 (FIGS. 2G, 2H). In one embodiment, the smooth segment of the cylindrical wall 21 extends into the interior cavity. In another embodiment, the rough segment extends into the interior cavity. In either case, the extension of either segment allows for a greater surface area and to accommodate pedicle screws of any size, width and shape.

In other embodiments, the cylindrical wall is continuous (FIGS. 2C-2F) having a smooth, non-threaded segment of the cylindrical wall which is inwardly and outwardly directed, that is, uniformly smooth. In other embodiments, the cylindrical wall is continuous (FIGS. 2C-2F) having a smooth, non-threaded segment of the cylindrical wall which is inwardly and outwardly directed and a rough segment having an inwardly or outwardly or both inwardly and outwardly directed rough surface. In other embodiments, the cylindrical wall comprises an outwardly directed smooth surface and an inwardly directed rough surface.

Figure 3C:
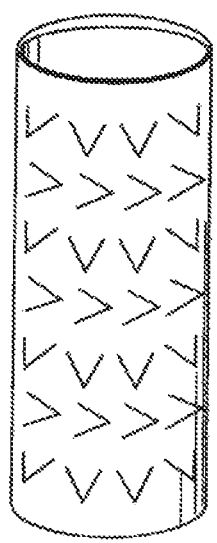
Figure 4:
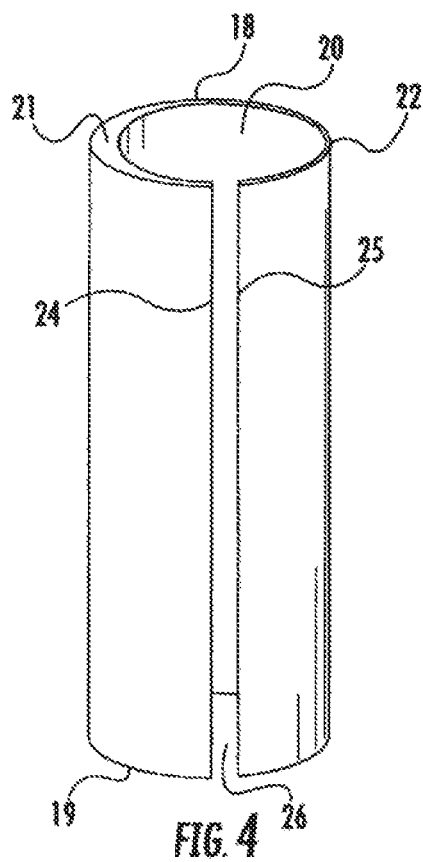
FIG. 4 is a segment view showing the cylindrical wall with a longitudinal slot extending from a first end to a second end, and having one segment of the cylindrical wall thicker than the other.
Figure 5:
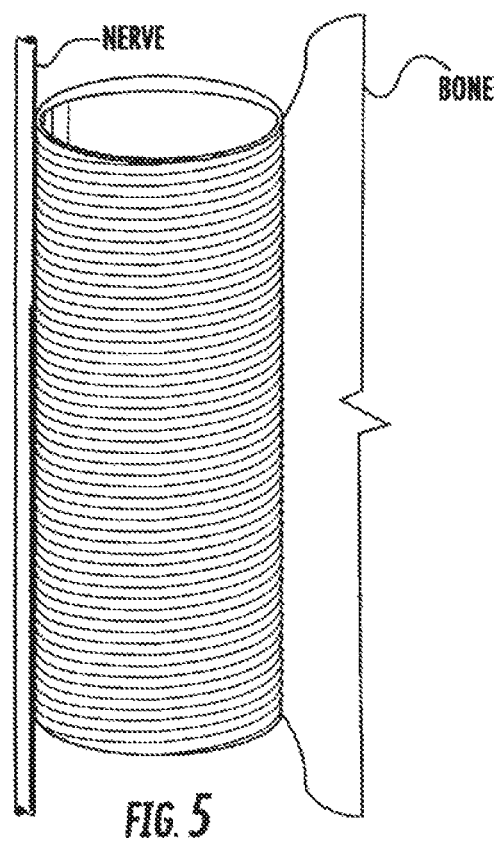
FIG. 5 is a segment view showing the cylindrical wall having one segment of the cylindrical wall smooth and thicker in width as compared to the opposing segment which is rough and thinner in width. The smooth thicker segment is placed to protect the nerve from the pedicle screw.

In embodiments wherein the pedicle insulator comprises a rough surface, the surface of the wall comprises threads (FIG. 3B), protrusions, teeth, barbs, fins or combinations thereof (FIGS. 3A, 3C).

In another embodiment, the pedicle insulator implant further comprises an outer cylindrical wall defining an interior cavity and having a first end and a second end. In some embodiments, the outer cylindrical wall comprises an inwardly directed smooth and non threaded surface, dimensioned to allow slidable insertion of the cylindrical wall.

In another embodiment, a pedicle insulator implant, implantable in a vertebral body of a spine, comprises a wall 12 defining an interior cavity 20 and having a first end IS and a second end 19. In one embodiment, the wall comprises a smooth and non-threaded inwardly and outwardly directed surface, or a smooth and non-threaded outwardly surface and a rough inwardly directed surface, a segment of the wall being of a thicker width than other segments of the wall. The wall can be of various shapes and can be dimensioned and shaped to fit pedicle screws of varying sizes and shapes. In one embodiment, the wall is non-continuous and comprises a longitudinal slot extending between the first end and the second end. In another embodiment, the wall is non-continuous and a segment of the wall extends within the hollow center, the inwardly directed surface of one segment 24 facing the outwardly directed surface 25 of an opposing segment. In another embodiment, the wall is cylindrical and continuous. In other embodiments, the segment of the wall comprising the thicker width comprises at least about 25% of the cylindrical wall surface area.

In another embodiment, an outer wall defining an interior cavity and having a first end and a second end. This outer wall comprises an inwardly directed smooth and non threaded surface, dimensioned to allow slidable insertion of the pedicle insulator implant (FIG. 1).

In another embodiment, a pedicle insulator implant assembly implantable into a vertebral body of a spine comprises: an inner wall 12 defining an interior cavity 20 having a first end 18 and a second end 19 (FIG. 1). The inner wall comprises a smooth surface segment, a rough surface segment or combinations thereof. In addition, the inner wall 12 comprises a segment of the inner wall which has a wider or thicker width as compared to other segments of the inner wall. In some embodiments the assembly comprises an outer wall 11 defining an interior cavity and having a first end 18 and a second end 19. The outer wall having an inwardly directed smooth and non threaded surface dimensioned to allow the inner wall to slidably fit into the outer wall.

In some embodiments, the inner wall 12 comprises: a longitudinal slot 23 extending between the first end 18 and the second end 19, a non-continuous wall and a segment of the wall 24,25 extends within the hollow center 20, a continuous wall or combinations thereof (FIGS. 2A-2H and 4).

In some embodiments, the pedicle insulator implant 12 is cylindrical, the distal end of the pedicle insulator implant being annularly tapered.

In some embodiments, the assembly further comprises a fixture sized and shaped to be inserted within a cavity defined by the inner wall of the pedicle insulator implant In some embodiments, the fixture is a pedicle screw.

In another embodiment, a method for stabilizing a surgical fixture comprises placing an implant at least partially about an intermediate segment of the fixture, the implant having a longitudinal slot and a segment of the implant having a thicker wall on one segment of the implant The distal end of the implant is driven into the tissue in which the fixture is inserted such that the thicker and smooth segment is located between the outer surface of the implant and a nerve or tissue to be protected. If desired, the implant comprises a segment of whereby the surface is rough, e.g. threaded, barbed etc., to provide further gripping of the implant to a bone. In some embodiments, the fixture is inserted into the tissue prior to the driving step. Placing of the implant comprises urging the intermediate segment of the fixture through the slot such that the fixture, e.g. a pedicle screw, is received within the cavity defined by the inner wall of the implant.

The unique features of the implant, e.g. the thicker smooth segment and a thinner segment, reduces a tendency of the fixture to toggle and also, increases pullout strength of the fixture.

The invention has been described in detail with reference to preferred embodiments thereof. However, it will be appreciated that those skilled in the art, upon consegmentration of this disclosure, may make modifications and improvements within the spirit and scope of the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All documents mentioned herein are incorporated herein by reference. All publications and patent documents cited in this application are incorporated by reference for all purposes to the same extent as if each individual publication or patent document were so individually denoted. By their citation of various references in this document. Applicants do not admit any particular reference is "prior art" to their invention.

What is claimed:

1. A method for stabilizing a surgical fixture comprising:
   inserting an implant into tissue, the implant comprising:
   a non-continuous cylindrical wall defining an interior cavity and having a first end and a second end;
   a first segment of the cylindrical wall comprising a smooth exterior surface;
   and
   a second segment of the cylindrical wall comprising a rough exterior surface, wherein:
   the first segment of the cylindrical wall is of a greater thickness than the second segment of the cylindrical wall; and
   a portion of the second segment of the cylindrical wall overlaps a portion of the first segment of the cylindrical wall, extending into the interior cavity; and
   driving a distal end of a fixture into tissue into which the implant is inserted.

2. The method of claim 1, wherein driving the distal end of the fixture into tissue into which the implant is inserted comprises urging an intermediate segment of the fixture through the interior cavity of the implant.

3. The method of claim 1, wherein the fixture is a pedicle screw.

4. The method of claim 1, wherein a distal end of the implant is annularly tapered.

5. The method of claim 1, wherein the implant further comprises a rough surface for enhancing grip of the fixture to a vertebra reducing the tendency of the fixture to toggle and increasing pullout strength of the fixture.

6. The method of claim 1, wherein the rough surface comprises threads, protrusions, teeth, barbs, fins, or combinations thereof.

7. The method of claim 6, wherein the rough surface comprises substantially triangular-shaped protrusions.

8. The method of claim 1, wherein the first segment of the implant comprises a first material and the second segment of the implant comprises a second material.

9. The method of claim 8, wherein the first material and the second material are biocompatible or bioinert materials.

10. The pedicle insulator implant of claim 9, wherein the second material is more ridged than the first material.

* * * * *